(12) United States Patent
Ryser

(10) Patent No.: US 6,848,633 B2
(45) Date of Patent: Feb. 1, 2005

(54) SPRAY DEVICE

(75) Inventor: Daniel Ryser, Stäfa (CH)

(73) Assignee: Tecan Trading AG, Mannedorf (CH)

( * ) Notice: Subject to any disclaimer, the term of this patent is extended or adjusted under 35 U.S.C. 154(b) by 0 days.

(21) Appl. No.: 10/132,607

(22) Filed: Apr. 25, 2002

(65) Prior Publication Data

US 2002/0179737 A1 Dec. 5, 2002

(30) Foreign Application Priority Data

Apr. 27, 2001 (EP) ............................................. 01810415

(51) Int. Cl.⁷ .............................................. B05B 7/06
(52) U.S. Cl. ...................... 239/424; 239/71; 239/340; 239/346; 239/418; 239/403; 239/590.5; 239/423; 422/100; 422/922; 73/864.11; 73/864.25; 73/864.81; 901/16; 901/46
(58) Field of Search ............................ 239/71, 86, 338, 239/340, 341, 346, 355, 357, 399, 403, 433, 423, 420, 424, 468, 590, 590.5, 600, 418; 422/100, 919, 922; 73/863.86, 864.11, 864.25, 864.81; 250/288; 901/14, 16, 30, 41, 46

(56) References Cited

U.S. PATENT DOCUMENTS

| | | | |
|---|---|---|---|
| 2,228,705 A | | 1/1941 | Olson |
| 4,977,785 A | * | 12/1990 | Willoughby et al. .......... 239/86 |
| 5,443,791 A | * | 8/1995 | Cathcart et al. ............ 422/100 |
| 5,464,157 A | * | 11/1995 | Bourdoulous et al. ...... 239/424 |
| 5,752,663 A | * | 5/1998 | Fischer et al. .............. 239/424 |
| 5,884,846 A | | 3/1999 | Tan |
| 5,935,523 A | * | 8/1999 | McCandless et al. ....... 422/100 |
| 6,032,876 A | * | 3/2000 | Bertsch et al. .............. 239/418 |
| 6,166,379 A | * | 12/2000 | Montaser et al. ........... 250/288 |
| 6,443,022 B1 | * | 9/2002 | Gordon .................... 73/864.25 |
| 6,478,238 B1 | * | 11/2002 | Wachs et al. ............... 239/338 |

FOREIGN PATENT DOCUMENTS

| | | |
|---|---|---|
| DE | 30 07 990 | 7/1981 |
| DE | 199 19 135 | 11/2000 |
| EP | 0 885 395 | 2/1997 |
| FR | 2 349 368 | 4/1976 |

* cited by examiner

Primary Examiner—Steven J. Ganey
(74) Attorney, Agent, or Firm—Notaro & Michalos P.C.

(57) ABSTRACT

In an aspirating and dispensing/spraying device, a holder is screwed onto a tube, connected to a liquid supply line, in such a way that it is displaceable along the tube by rotation. The tube is surrounded at a distance by a coaxial sleeve, which is solidly anchored in the holder, having a discharge opening on its front end, which is conically narrowed, whose edge surrounds the front end of the tube, which carries a outlet opening, separated by a narrow annular gap from the tube. The sleeve carries a connecting piece laterally, to which a pressurized gas supply line is connected and which discharges eccentrically into the space between the sleeve and the tube, so that pressurized gas flowing in receives angular momentum. When the gas flows out of the annular gap, it mixes intensively with the liquid coming out of the outlet opening and forms a discharge cone made of a fine, symmetrical aerosol with the liquid. This aspirating and dispensing/spraying device is simultaneously implemented as a pipette for aspirating liquids through the outlet opening of the tube's front end, said tube carrying a sensor near said outlet opening for detecting a liquid surface during pipetting.

15 Claims, 3 Drawing Sheets

Fig. 3
Fig. 4
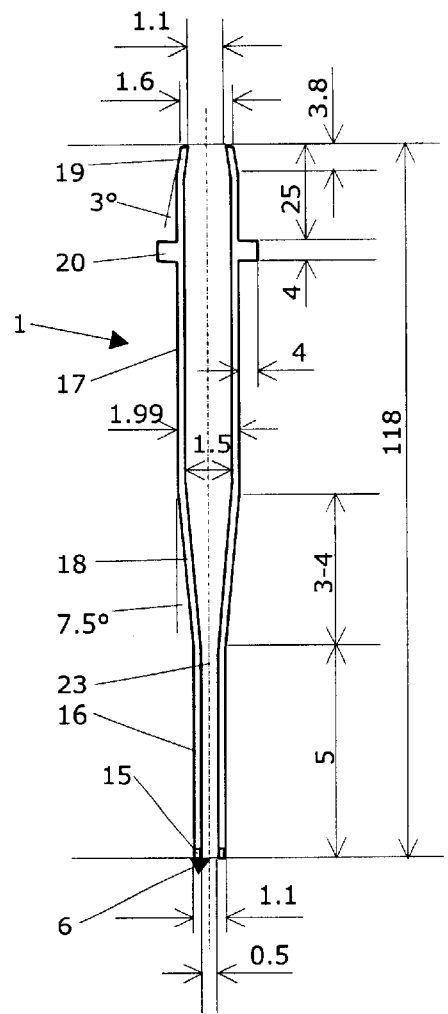
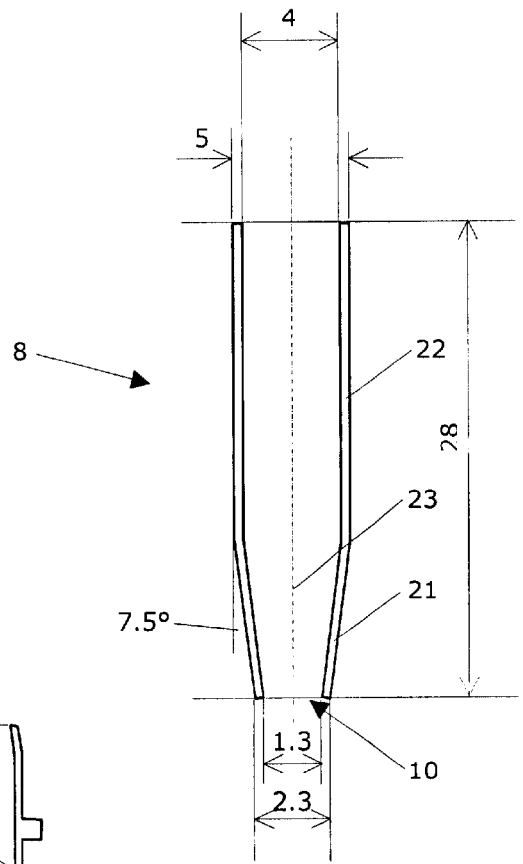
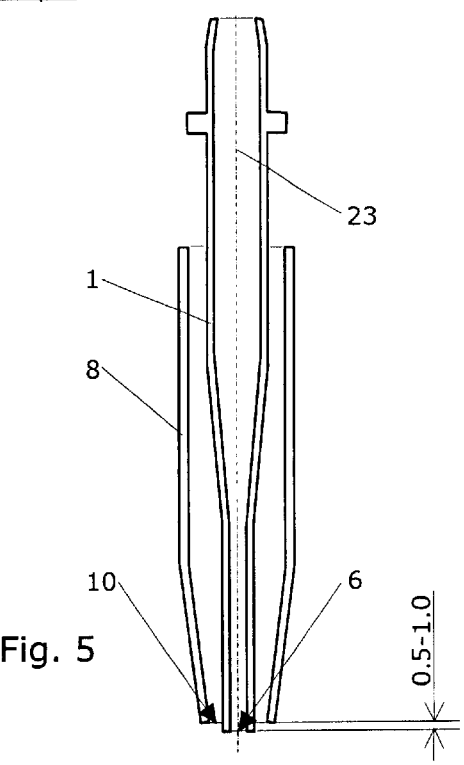
Fig. 5

SPRAY DEVICE

RELATED APPLICATION DATA

This application claims priority of the European patent application No. 01 810 415.8 filed on Apr. 27, 2001, the entire disclosure of which is incorporated herein by reference.

FIELD OF THE INVENTION

The present invention relates to an aspirating and dispensing/spraying device for a laboratory device, e.g. for a pipettor, in which the aspirating and dispensing/spraying device may be used. It may be used for keeping gels or membranes moist or also for spraying plants or plant parts, such as leaves, larva, etc., with diverse liquids.

BACKGROUND OF THE INVENTION

Aspirating and dispensing/spraying devices are known which are implemented like watering cans having small openings distributed over a surface. These types of aspirating and dispensing/spraying devices are spray devices and are subject to various disadvantages, which, above all, impair the possibilities for their use in the laboratory field. Thus, it is not possible, particularly with changing pressures, to ensure uniform distribution of the liquid over a larger area, particularly if the openings are relatively large, so that the individual streams are not sufficiently dispersed. On the other hand, if the openings are very small they clog easily, which in turn impairs the uniformity of the distribution or makes any proper functioning impossible. In addition, these types of spray devices are relatively complicated and expensive to produce under certain circumstances.

Spray devices are known from U.S. Pat. No. 5,884,846 which are used to inject liquids into an inductively coupled plasma spectrometer (ICP). In this case, the liquids are supplied from a reservoir via a capillary and, either via the supply pressure and/or merely by the suction produced by the annular gas nozzle surrounding the capillary, atomized into a fog and/or aerosol and continuously dispensed at a predetermined rate. The relative position of the gas nozzle opening, which is coaxially displaceable in relation to the capillary opening, is decisive for the aerosol formation in this case. If very small but reproducible quantities of liquid, e.g. an exactly defined quantity of a few $\mu l$ at a time, are to be dispensed, this system is not suitable, because it does not support the required mode of operation.

Aspirating and dispensing/spraying devices in a testing system for chemical materials or material mixtures are known from European Patent 0 885 395, which function either according to the principle of a spray pistol (cf. U.S. Pat. No. 5,884,846) or according to the principle of an inkjet printer. In a first embodiment, the liquid to be sprayed is poured into a reservoir, from which the liquid is atomized using the suction of a gas nozzle. Alternatively to this, micropipettes are disclosed, in a second embodiment, with which a certain quantity of liquid may first be aspirated. With the aid of piezoelectric transducers, extremely fine droplets are generated which are exactly controllable in regard to their size and target, so that the droplets are dispensed like an inkjet printer. The "spray pistol" does allow the delivery of more or less defined quantities (typically 10–100 $\mu l$), but the mode of operation is considered cumbersome and therefore time-consuming. The "inkjet printer" allows dispensing of individual fine droplets, but an aerosol may not be generated, so that the "drizzling" of larger surfaces is also time-consuming. In addition, this technology appears complicated and expensive.

SUMMARY OF THE INVENTION

The present invention is based on the object of providing a simple aspirating and dispensing/spraying device for laboratory devices, particularly in a testing and/or processing system for chemical materials or material mixtures, which is not susceptible to malfunctions and reliably ensures uniform distribution of a defined liquid sample. This object is achieved by the aspirating and dispensing/spraying device as it is characterized in Claim 1. An aspirating and dispensing/spraying device for a laboratory device, particularly in a testing and/or processing system for chemical materials or material mixtures, is suggested having a tube—whose front end has an outlet opening for delivery of a liquid and to whose back end a liquid supply line is connected—, having a sleeve which encloses the tube at a distance and having a pressurized gas supply line for supplying pressurized gas into a space lying between the sleeve and the tube, the sleeve having a discharge opening on the front end in which the front end of the tube is positioned in such a way that an annular gap which ensures the release of pressurized gas remains free between the tube and the edge of the discharge opening. The aspirating and dispensing/spraying device according to the present invention is characterized in that it is also implemented as a pipette for picking up liquids. Preferred refinements and additional features of the aspirating and dispensing/spraying device according to the present invention result from the dependent claims. The aspirating and dispensing/spraying device according to the present invention is not only very reliable, it also ensures intensive mixing of liquid and gas and therefore the formation of a very fine aerosol, which is distributed symmetrically over a discharge cone. In addition, it is simply constructed and economically producible. It may also be designed in such a way that the shape of the discharge cone is adjustable within specific limits. Another advantage in relation to the related art is that, using the aspirating and dispensing/spraying device according to the present invention (preferably guided by a robot arm and equipped with automatic liquid level detection), liquid samples having a defined volume may be purposely aspirated from any desired location, e.g. from a well of a 96-well microplate, and immediately sprayed out again, without modification or repipetting, at any desired location, e.g. in a well of another microplate or on a surface (e.g. on a gel, a plant part, etc.

BRIEF DESCRIPTION OF THE DRAWINGS

In the following, the present invention is described in more detail with reference to figures which merely represent one exemplary embodiment.

FIG. 3 shows a longitudinal section through a tube of a preferred embodiment;

FIG. 4 shows a longitudinal section through a sleeve of a preferred embodiment;

FIG. 5 shows a longitudinal section through a tube of a preferred embodiment inserted into a sleeve;

DETAILED DESCRIPTION OF THE INVENTION

Figure 1:
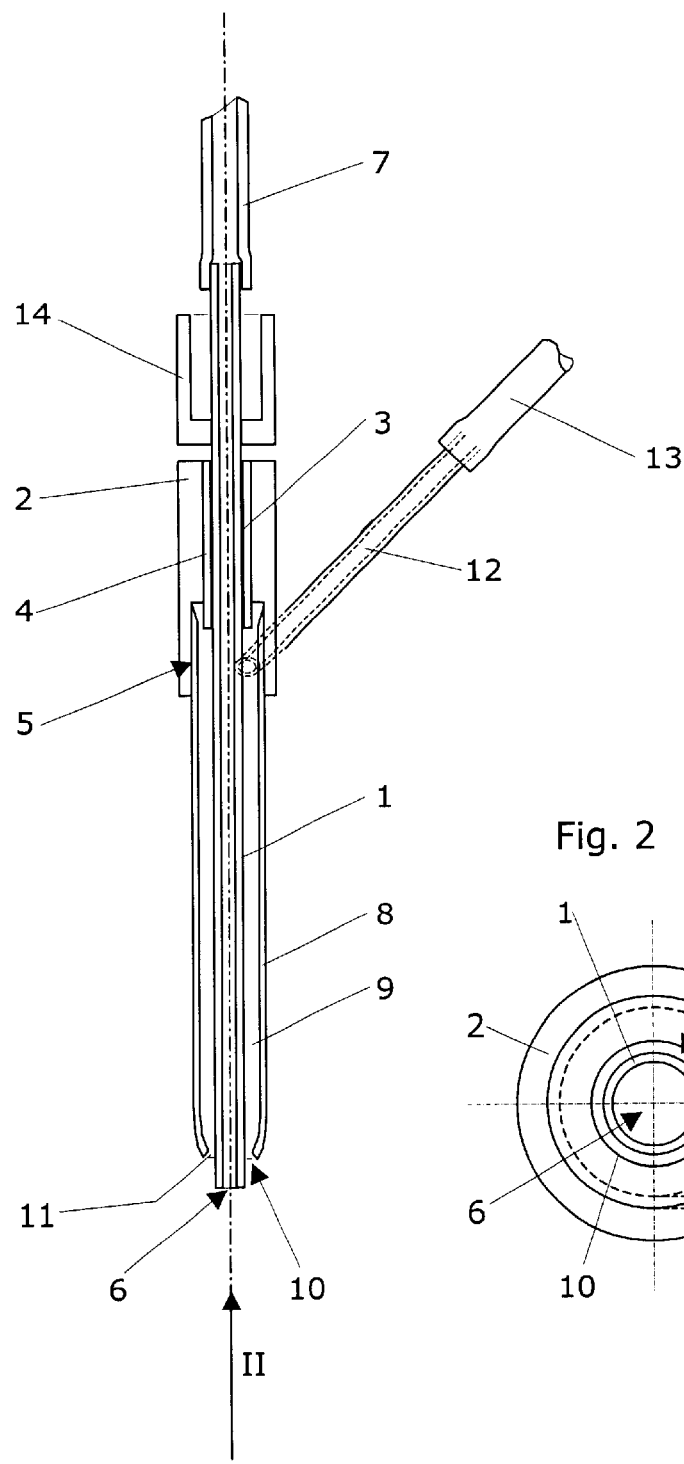
FIG. 1 shows a longitudinal section through an aspirating and dispensing/spraying device according to the present invention.
Figure 2:
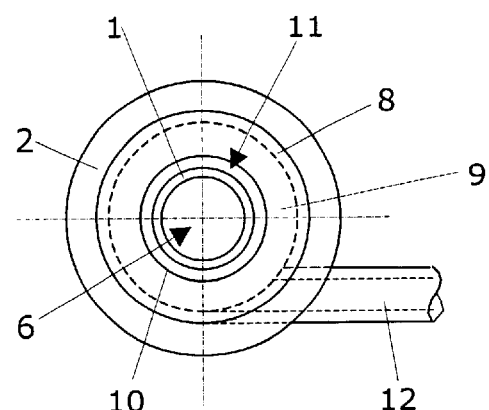
FIG. 2 shows a slightly enlarged view of the aspirating and dispensing/spraying device from FIG. 1 from below, in the direction of arrow II.

The aspirating and dispensing/spraying device has a tube 1, onto which an approximately cylindrical holder 2 is also screwed, an outer thread 3 on tube 1 engaging with the thread of a threaded bore 4 of holder 2 which receives it, which opens into a coaxial cylindrical recess 5 on the bottom of holder 2. The holder may therefore be displaced along tube 1 by rotation. Its forward end, which is further from recess 5, carries a outlet opening 6, while its back end, which lies above holder 1, adjoins a tube 7 which connects it to, for example, a liquid container and which is used as a liquid supply line.

A sleeve 8 is solidly anchored in recess 5 which is also implemented as essentially tubular and surrounds tube 1 coaxially at a distance, so that a space 9 approximately in the shape of a cylinder envelope lies between the inside of sleeve 8 and the outside of tube 1. Sleeve 8, and therefore space 9, narrow approximately conically toward the front end of tube 1 to a discharge opening 10, in which the front end of tube 1 lies approximately even with outlet opening 6, and in such a way that tube 1 is surrounded there by the edge of discharge opening 10 at a slight distance, so that a narrow peripheral annular gap 11 remains free. By displacing holder 2 as described above, sleeve 8, and therefore discharge opening 10, may be axially displaced. The latter may lie at approximately the same level as the front end of tube 1. However, discharge opening 10 usually is offset upward somewhat, so that the front end of tube 1 having outlet opening 6 projects slightly out of discharge opening 10.

A connecting piece 12, which is in one piece with sleeve 8, also opens into sleeve 8 in the region of recess 5 and is guided through an opening or a slot in the part of holder 2 which forms the side wall of recess 5. Connecting piece 12 is bent somewhat, so that it encloses an acute angle with the part of sleeve 8 lying above its mouth. In addition, it is laterally offset so that it is not aligned toward the shared axis of sleeve 8 and tube 1, but discharges approximately tangentially into space 9, which is shaped like a cylinder envelope. Connecting piece 12 is used as a pressurized gas supply line.

A hose 13, which connects it to, for example, a pressurized gas tank or a filter facility and a pump, is connected to its end. An adapter 14, also approximately cylindrical, is attached above holder 2 on tube 1, using which the aspirating and dispensing/spraying device may be attached toga robot arm or the like of, for example, a pipettor, so that it is displaceable at least vertically (in the Z direction), but preferably also horizontally (in the X and/or Y direction).

Tube 1, holder 2, and sleeve 8, including connecting piece 12, are preferably made of stainless steel, and adapter 14 is made of anodized aluminum. Hoses 7 and 13 may be implemented as plastic hoses. Tube 1 may, for example, have an approximately 1.4 mm internal diameter and 2 mm external diameter, and the sleeve may have an approximately 3.4 mm internal diameter and 4 mm external diameter. Annular gap 11 may be between 0.05 mm and 0.15 mm wide, its width is preferably approximately 0.1 mm.

FIG. 3 shows a longitudinal section through a tube 1 of a preferred embodiment of the aspirating and dispensing/spraying device according to the present invention. This tube 1, which is preferably produced in one piece, includes a front cylindrical part 16 and a back cylindrical part 17, which are connected to one another by a first conical part 18. A second conical part 19 sits on the upper end of tube 1 and makes slipping on a hose 7 easier due to its reduction of the tube cross-section. Tube 1 also has an annular rib 20, which is used as a stop. Tube 1 preferably carries a sensor 15 near its outlet opening 6 for detecting the liquid surface (liquid level detection) during pipetting. Particularly preferred manufacturing dimensions are indicated in FIG. 3.

FIG. 4 shows a longitudinal section through a sleeve 8 of a preferred embodiment of the aspirating and dispensing/spraying device according to the present invention. This sleeve includes a conical part 21, which opens into discharge opening 10, and a cylindrical part 22 which adjoins it. Particularly preferred manufacturing dimensions are indicated in FIG. 4.

FIG. 5 shows a longitudinal section through a tube 1, inserted into a sleeve 8, of a preferred embodiment of the aspirating and dispensing/spraying device according to the present invention. In this case, tube 1 and sleeve 8 are positioned co-axially to essentially vertical longitudinal axis 23. The distance between outlet opening 6 of tube 1 and discharge opening 10 of sleeve 8 is preferably 0.5 to 1 mm during aspiration of a liquid. In addition, it has been shown that this configuration is particularly well suitable for both aspirating and dispensing (spraying). Depending on the desired spray field diameter and/or working distance, it may, however, be appropriate to adjust the dimensions indicated. Thus, it may be provided that particularly the distance between outlet opening 6 of tube 1 and discharge opening 10 of sleeve 8 is varied, which is preferably performed automatically via the computer control (possibly having an additional distance sensor) and a drive suitable for the coaxial displacement of the sleeve.

In use, liquid to be sprayed, e.g. water or a pesticide or the like, is supplied through hose 7 and tube 1 to outlet opening 6 and pressurized gas, e.g. air, nitrogen, or carbon dioxide, is supplied through connecting piece 12 into space 9, so that a pressurized gas flow arises in the space directed toward discharge opening 10, which is distinguished by angular momentum due to its eccentric introduction. The pressurized gas flowing out of annular gap 11 generates a partial vacuum in the region of outlet opening 6, so that liquid comes out of it which intensively mixes with the pressurized gas. The pressurized gas and the liquid therefore form a fine, well mixed aerosol stream which symmetrically diverges in a cone. The composition and included angle of the cone may be adjusted over a relatively wide range via the gas pressure and through adjustment of the axial position of discharge opening 10 relative to outlet opening 6.

Figure 7A:
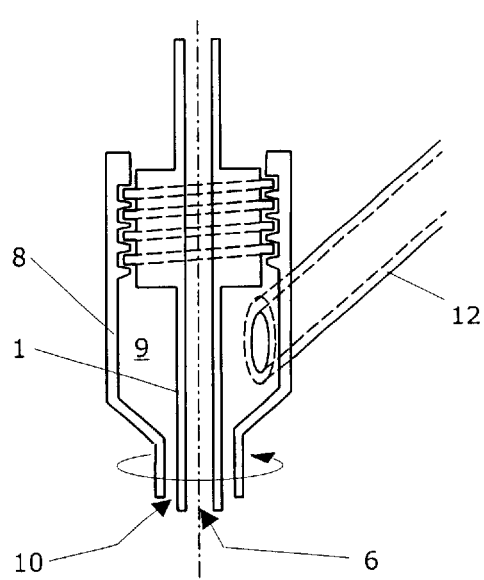
FIG. 7 shows alternative embodiments according to the invention.
Figure 7B:
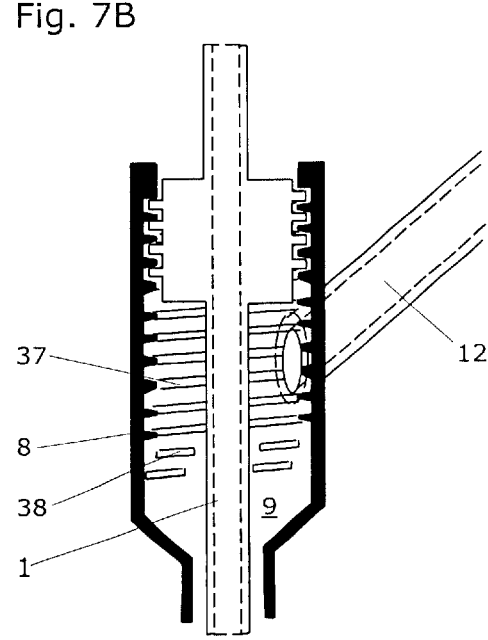

Various alternatives to the exemplary embodiment described are possible without leaving the basic idea of the present invention. Thus, the tube may be approximately centered by a sliding guide, positioned near the discharge opening in the (see FIG. 7A). The angular momentum applied to the pressurized gas may be produced in other ways than that described, e.g. by slanted ribs 37 or wings 38 (see FIG. 7B) positioned in the space, and a sliding guide like the one mentioned above may possibly also be made of ribs of this type and therefore simultaneously be used to generate the angular momentum. Deviations from the materials and dimensions indicated above are also possible.

Figure 6:
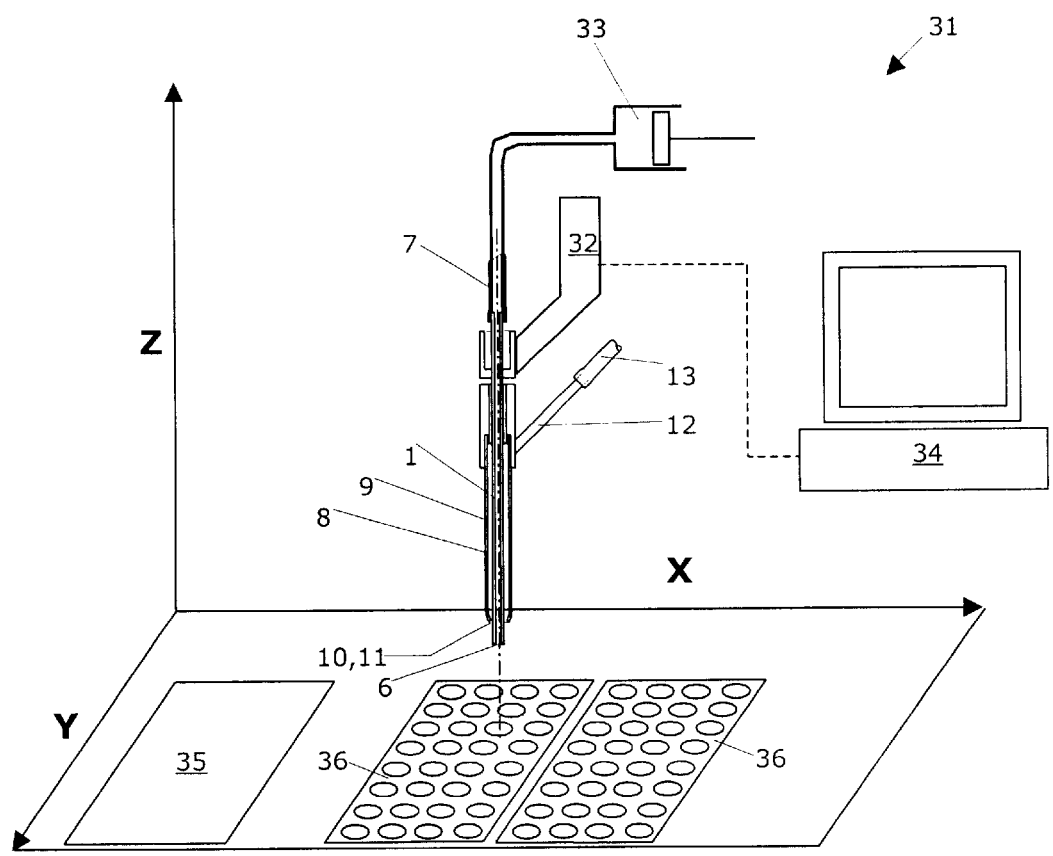
FIG. 6 shows an arrangement of a testing and/or processing system for chemical materials or material mixtures that includes one aspirating and dispensing/spraying device according to the invention.

FIG. 6 shows an arrangement of a testing and/or processing system for chemical materials or material mixtures that includes one aspirating and dispensing/spraying device according to the invention. The aspirating and dispensing/spraying device according to the present invention is preferably installed individually or in groups, i.e., in linear or planar arrays, in a testing and/or processing system for chemical materials or material mixtures, in which these aspirating and dispensing/spraying devices may be used for aspirating and/or dispensing liquid samples. Such testing and/or processing systems 31 preferably include at least one robot arm 32, to which the aspirating and dispensing/spraying device(s) is/are connected so they are movable in the X and/or Y and/or Z directions. Such laboratory systems are preferably equipped with a computer 34 for controlling and checking the movements of the robot arm 32, the liquid level detection sensor and/or liquid sensor, and the aspirating and dispensing/spraying devices, and preferably with one piston pump 33 per aspirating and dispensing/spraying device for aspirating liquid samples. Piston pumps for high precision aspiration and dispensing of liquids, such as commercially available devices having the names "CAVRO XL 3000 Modular Digital Pump" and/or "CAVRO XP 3000 plus Modular Digital Pump", which are distributed by the firm Tecan Systems Inc., 2450 Zanker Road, San Jose, Calif. 95131 USA (formerly Cavro Scientific Instruments Inc.) are preferred. These pumps 33 are connected via a liquid line 7 to the back end of tube 1. The computer 34 is preferably equipped with a monitor and may be a part of a testing and/or processing system for chemical materials or material mixtures or may be provided separately. The chemical materials or material mixtures are preferably tested and/or processed at a temperature between 0° C. and 100° C., particularly preferably at room temperature. Liquid samples having a defined volume may be purposely aspirated from any desired location, e.g. from a well of a 96-well microplate 36, and immediately sprayed out again, without modification or repipetting, at any desired location, e.g. in a well of another microplate 36 or on a surface 35 (e.g. on a gel, a plant part, etc.).

List of Reference Numbers

1 tube
2 holder
3 external thread
4 threaded bore
5 recess
6 outlet opening
7 hose
8 sleeve
9 space
10 discharge opening
11 annular gap
12 connecting piece
13 hose
14 adapter
15 sensor for liquid level detection
16 front cylindrical part of 1
17 back cylindrical part of 1
18 first conical part of 1
19 second conical part of 1
20 annular rib of 1
21 conical part of 8
22 cylindrical part of 8
23 vertical axis
31 testing and/or processing system
32 robot arm
33 piston pump
34 computer
35 surface
36 microplate
37 slanted ribs
38 slanted wings

What is claimed is:

1. An aspirating and dispensing/spraying device for use in a laboratory device, particularly in a testing and/or processing system for chemical materials or material mixtures, the aspirating and dispensing/spraying device having a tube whose front end has an outlet opening for dispensing a liquid sample that is introduced into this tube and to whose back end a liquid supply line is connected, the aspirating and dispensing/spraying device having a sleeve which encloses the tube at a distance and having a pressurized gas supply line for supplying pressurized gas into a space lying between the sleeve and the tube, the sleeve having a discharge opening on the front end in which the front end of the tube is positioned in such a way that an annular gap which ensures the release of pressurized gas remains free between the tube and the edge of the discharge opening, the aspirating and dispensing/spraying device thus forming a device for spraying the liquid sample by intensively mixing it with the gas, wherein the aspirating and dispensing/spraying device is implemented as a pipette for aspirating liquid samples through the outlet opening of the tube's front end, said tube carrying a sensor near said outlet opening for detecting a liquid surface during pipetting.

2. The aspirating and dispensing/spraying device according to claim 1, wherein the sleeve is essentially rotationally symmetric and narrows toward the discharge opening.

3. The aspirating and dispensing/spraying device according to claim 1, wherein a threaded bore rigidly connected to the sleeve engages with an external thread on the tube in such a way that the sleeve is displaceable along the tube by rotation.

4. The aspirating and dispensing/spraying device according to claim 1, wherein it has a holder mounted on the tube, on which the sleeve is attached.

5. The aspirating and dispensing/spraying device according to claim 1, wherein the pressurized gas supply line includes a connecting piece which is in one piece with the sleeve and projects laterally from it.

6. The aspirating and dispensing/spraying device according to claim 1, wherein at least the tube and the sleeve are made of stainless steel.

7. The aspirating and dispensing/spraying device according to claim 1, wherein the pressurized gas line or its connection to the space forming the annular gap is implemented in such a way that the pressurized gas coming out has angular momentum applied to it.

8. The aspirating and dispensing/spraying device according to claim 7, wherein the pressurized gas supply line opens into the space between the tube and the sleeve eccentric to the axis of the tube.

9. The aspirating and dispensing/spraying device according to claim 7, wherein slanted ribs or wings are positioned in the space.

10. The aspirating and dispensing/spraying device according to claim 9, wherein the slanted ribs in the space are additionally implemented as a sliding guide for the sleeve.

11. The aspirating and dispensing/spraying device according to claim 1, wherein an adapter is connected to the tube for attachment of the aspirating and dispensing/spraying device to a robot arm of a laboratory device movable in at least the Z direction.

12. A testing and/or processing system for chemical materials or material mixtures, which includes one or more aspirating and dispensing/spraying devices according to claim 1.

13. The testing and/or processing system according to claim 12, which includes at least one robot arm to which the aspirating and dispensing/spraying devices are connected so they are movable in the X and/or Y and/or Z directions.

14. A testing and/or processing system for chemical materials or material mixtures which includes one or more aspirating and dispensing/spraying devices for aspirating and/or dispensing liquid samples, in which each aspirating and dispensing/spraying device has a tube whose front end has an outlet opening for dispensing a liquid sample that is introduced into this tube and to whose back end a liquid supply line is connected, the aspirating and dispensing/spraying device having a sleeve which encloses the tube at a distance and having a pressurized gas supply line for supplying pressurized gas into a space lying between the sleeve and the tube, the sleeve having a discharge opening on the front end in which the front end of the tube is positioned in such a way that an annular gap which ensures the release of pressurized gas remains free between the tube and the edge of the discharge opening, the aspirating and dispensing/spraying device thereby spraying the liquid sample by intensively mixing it with the gas, the pressurized gas line or its connection to the space forming the annular gap is implemented in such a way that the pressurized gas coming out has angular momentum applied to it, wherein the aspirating and dispensing/spraying device is implemented as a pipette for aspirating liquid samples through the outlet opening of the tube's front end, said tube carrying a sensor near said outlet opening for detecting a liquid surface during pipetting.

15. The testing and/or processing system according to claim 14 which includes at least one robot arm to which aspirating and dispensing/spraying devices are connected so they are movable in the X and/or Y and/or Z directions.

* * * * *